United States Patent [19]
Privette et al.

[11] Patent Number: 5,475,019
[45] Date of Patent: Dec. 12, 1995

[54] METHOD OF TREATING ANXIETY-RELATED DISORDERS WITH 2-AMINOCYCLOALIPHATIC AMIDE COMPOUNDS

[75] Inventors: Thomas H. Privette; David M. Terrian, both of Greenville, N.C.

[73] Assignee: East Carolina University, Greenville, N.C.

[21] Appl. No.: 14,776

[22] Filed: Feb. 8, 1993

[51] Int. Cl.⁶ .................................................. A61K 31/40
[52] U.S. Cl. ........................ 514/408; 514/409; 514/411
[58] Field of Search ...................... 514/408, 409, 514/411

[56] References Cited

U.S. PATENT DOCUMENTS

| | | | |
|---|---|---|---|
| 4,098,904 | 7/1978 | Szmuszkovicz | 424/324 |
| 4,145,435 | 3/1979 | Szmuszkovicz | 424/274 |

FOREIGN PATENT DOCUMENTS 2225325  5/1990  United Kingdom.

OTHER PUBLICATIONS

M. Gue et al., American Journal of Physiology; 254 (6,Pt.1) G802–G807 (1988).
M. Takahashi et al.; Japan J. of Pharmacol.; 53,487–494 (1990).
C.A.: vol. 111 (23); #209368F; Bueno et al. (1989).
C.A.: vol. 112 (1); #1000t; Gue et al. (1990).
B. J. Pleuvry, British Journal of Anaesthesia 66, 370–380 (1991).

Primary Examiner—T. J. Criares
Attorney, Agent, or Firm—Bell, Seltzer, Park & Gibson

[57] ABSTRACT

A method for combatting anxiety in a subject in need of such treatment is provided. The method comprises administering to the subject a 2-aminocycloaliphatic amide kappa opioid agonist in an effective anxiety-combatting amount.

6 Claims, 2 Drawing Sheets

METHOD OF TREATING ANXIETY-RELATED DISORDERS WITH 2-AMINOCYCLOALIPHATIC AMIDE COMPOUNDS

This invention was made with Government support under Grant No. AFOSR-89-0531 awarded by the Air Force Office of Scientific Research. The Government has certain rights in this invention.

FIELD OF THE INVENTION

This invention relates generally to methods for treating anxiety in subjects in need of such treatment, and more specifically relates to treating anxiety by administering a kappa opioid receptor agonist to such a subject.

BACKGROUND OF THE INVENTION

Anxiety and anxiety-related disorders are extremely common. Anxiety-related conditions can be relatively mild or can be sufficiently severe as to be quite disabling. Also noteworthy is that anxiety, while infrequently a "disease" in itself, is an almost inevitable and often exacerbating consequence of many other medical and surgical conditions.

The most common treatment for anxiety is to administer one of a class of anxiolytic agents. The most common of these are benzodiapenes such as diazepam and alprazolam. Benzodiapenes can act to counteract anxiety by depressing the electrical afterdischarge in the limbic system, and may possibly inhibit neurotransmission mediated by gamma-aminobutyrate (GABA). Gilman et al., *The Pharmaceutical Basis of Therapeutics* 434 (Gilman et al., eds., 7th ed., McMillan Publishing Co., New York 1985). These compounds have proven to be effective at reducing anxiety, but they also have significant depressant effects and act as skeletal muscle relaxers. These side effects can render these compounds unsuitable for many patients, particularly those whose anxiety is coupled to another form of illness.

British Patent No. 2 225 325 to Gozzini et al. discloses an opioid peptide with high affinity for delta opioid receptors. Administration of the peptide is said to control pain and the symptoms of depression and anxiety. No mention is made therein of reduced sedative effects.

In view of the foregoing, it is an object of the present invention to provide new treatment methods for combatting the effects of anxiety, along with compositions for carrying out the same.

SUMMARY OF THE INVENTION

These and other objects are satisfied by the present invention, which as a first aspect comprises a method of treating anxiety in a subject in need of such treatment by administering a kappa opioid receptor agonist (the "active compound agent") to such a subject in an amount effective to combat anxiety. Preferably, the subject is a human subject. Preferably, the compound is a compound of formula I

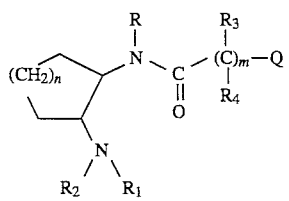

(I)

wherein:

R is C1 to C3-alkyl;

R1 is C1 to C3-alkyl, and R2 is C1 to C6-alkyl, —CH2CF3, C3 to C6-(allylic)alkenyl, C2 to C5-hydroxyalkyl, C3 to C6-cycloalkyl, C3 to C4-cycloalkylmethyl, phenyl-C1 to C3-alkyl, or alternatively R1 and R2 together with the nitrogen atom to which they are bonded form a saturated, monocyclic, heterocyclic ring containing only carbon and nitrogen ring atoms and containing from 3 to 4 carbon atoms, the said saturated monocyclic heterocyclic ring being optionally substituted in the 3-position of the ring with hydroxy, C1 to C3 alkyl, C1 to C3-alkyloxy, or C1 to C3-alkanoyloxy;

R3 is hydrogen or methyl;

R4 is hydrogen or methyl, or R3 and R4 together with the carbon atom to which they are bonded form a cyclopropylene ring;

m is 1 to 4;

n is 2 to 4; and

Q is 1-naphthyl, 2-naphthyl or a moiety of formula II

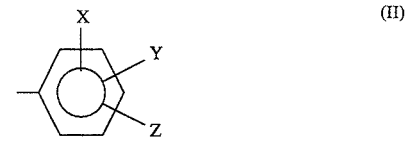

(II)

wherein each of X, Y and Z is hydrogen, a halogen having an atomic number of from 9 to 35, trifluoromethyl, C2 to C3-alkyl, C1 to C3-alkyloxy, azido or phenyl, and at least one of X, Y and Z is a substituent other than hydrogen, and when one of X, Y and Z is azido, phenyl, C1 to C3-alkyloxy or trifluoromethyl, the remaining X, Y and Z moieties are hydrogen; and the pharmaceutically acceptable salts thereof. It has been discovered that the administration of a kappa opioid receptor agonist can combat anxiety. Preferably, the administered compound is a compound of formula I, which has the particular advantage of having reduced or no sedative effect on the subject.

A second aspect of the present invention is the use of an active compound as given above for the preparation of a medicament for the treatment of anxiety, as described herein.

DETAILED DESCRIPTION OF THE INVENTION

Figure 1:
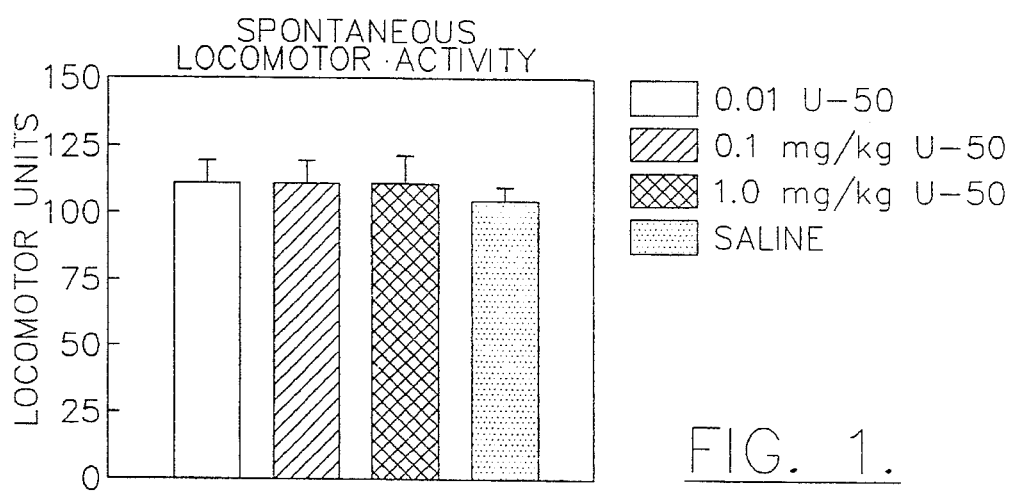
FIG. 1 is a bar graph showing the spontaneous locomotor activity of rats in the open cell test administered one of three different dosages of U-50,488H or saline. Note that U-50,488H is referred to as U-50 in the figure legends.

As used herein, the term "anxiety" is intended to refer to a condition of apprehension, uncertainty, dread, or fear unattached to a clearly defined stimulus accompanied by numerous physiological and psychological symptoms such as tachycardia, dyspnia, tension, restlessness, inattentiveness, and loss of appetite, skeletal motor function, initiative, cognitive logic, short- and long-term memory, and the like. Practice of the method of the present invention can combat, i.e., reduce or alleviate, some, most, or all of these physiological symptoms.

A suitable subject to be treated by the present method is an animal, such as a human or other mammal (e.g., house pets such as dogs and cats, or other commercially valuable or domestic animals), which experience anxiety-related symptoms due to some external or internal stimulus that are desirably combatted. Preferably, the subject is human.

A kappa opioid receptor is but one of at least three recognized types of opioid receptors present in the central nervous system, the others being mu receptors and delta receptors, each of which is so designated for historical reasons. Kappa receptors are generally found in areas of the brain associated with pain perception and regulation of water balance and food intake, and administration of agonists for kappa receptors have shown analgesic effects. Kappa opioid receptors agonists selectively and stereospecifically bind kappa opioid receptor agonists as opposed to agonists of mu and delta receptors, which have essentially no affinity for kappa opioid receptors. Pleurvy, *Brit. J. Anasthesia* 66:370–380 (1991). Thus, kappa opioid receptor agonists employed in carrying out the present invention are administered at a dosage effective to evoke an anxiolytic response mediated by the kappa opioid receptor, but essentially ineffective to evoke any anxiolytic response mediated by delta or mu opioid receptor.

As a result of the inventors' research, it has been discovered that the administration of agonists selective for kappa opioid receptors can combat anxiety in subjects in need of such treatment. Exemplary agonists include: the peptide products and active fragments of the prohormone prodynorphin, which include dynorphins such as dynorphin 1–13, dynorphin 1–9, dynorphin 1–17, and dynorphin 1–8, as well as leumorphin and beta-neo-morphin; azocines such as ketocyclazocine, ethylketocyclazocine, bremazocine, and pentazocine; tifluadom; U-62,066; U-69,593; MR 2034; nalorphine; pentazocine; buprenorphine; BC 3016; compounds of formula I above, wherein R, $R_1$, $R_2$, $R_3$, $R_4$, Q, X, Y, and Z are as defined above, and the pharmaceutically acceptable salts thereof. As used herein to refer to prodynorphin products, "active fragments" are peptides derived from these products which have N-terminal, C-terminal, or both N-terminal and C-terminal residues deleted, but nevertheless retain the biological activity of the products as described herein.

For compounds of formula I, it is preferred that R be methyl. It is also preferred n be equal to 2, and that m be equal to 1. $R_3$ and $R_4$ are preferably hydrogen.

$R_1$ and $R_2$ preferably together with the nitrogen atom to which they are bonded form a saturated monocyclic heterocyclic ring containing only carbon atoms and nitrogen atoms. The ring can be optionally substituted at the 3-position with hydroxy, C1 to C3-alkyl, C1 to C3-alkoxy-, or C1 to C3-alkanoyloxy, although preferably the ring is unsubstituted. In a particularly preferred embodiment, $R_1$ and $R_2$ form a pyrrolidinyl moiety.

Q is preferably a compound of formula II in which at least one of X, Y, and Z is a halogen having an atomic number of from 9 to 35. More preferably, Q is 3, 4-dicholorophenyl.

The compounds of formula I can be stereoconfigured so that the nitrogen atom bound to $R_1$ and $R_2$ and the amide nitrogen are on the same side of the cycloaliphatic ring (the cis- configuration) or on opposite sides (the trans- configuration). Preferably, the compounds of formula I are in the trans-configuration.

A particularly preferred compound of Formula I is trans-N-[2-(1-pyrrolidinyl)cyclohexyl]-N-methyl- 2-(3,4-dichlorophenyl) acetamide, which is shown in formula III.

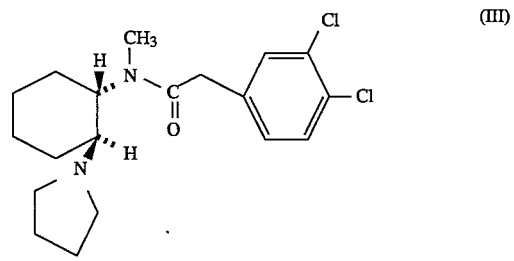

Compounds of Formula I and their preparation are known and are set forth in detail in U.S. Pat. No. 4,145,435, issued 20 Mar. 1979 to Szmuszkovicz, the content of which is incorporated herein by reference in its entirety.

The preparation of prodynorphin products and active fragments thereof is known to those skilled in this art. They may be produced by recombinant means in cells which do not typically produce these products, and by culture of cells which ordinarily produce these products, either in the form of the prohormone prodynorphin or the active products thereof.

Techniques for the preparation of the azocines, tifluadom, nalorphine, and buprenorphine are known to those skilled in this art.

The present invention extends to non-physiologically acceptable salts of the selective agonists of kappa opioid receptors which may be used in the preparation of the pharmacologically active compounds of the invention. The physiologically acceptable salts of kappa opioid receptor agonists include salts derived from bases. Base salts include ammonium salts, alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

In the manufacture of a medicament according to the invention, hereinafter referred to as a "formulation," the kappa opioid receptor agonists and the physiologically acceptable salts thereof, or the acid derivatives of either thereof (referred to as the "active compound") are typically admixed with, among other things, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more active compounds may be incorporated in the formulations of the invention, which may be prepared by any of the well known techniques of pharmacy consisting essentially of admixing the components.

The formulations of the invention include those suitable for oral, rectal, topical, buccal (e.g., sublingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like.

Capsules, both hard and soft, are filled with compositions of these amino-amide active ingredients in combination with suitable diluents and excipients, for example, edible oils, talc, calcium carbonate and the like, and also calcium stearate.

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Liquid preparations for oral administration are prepared in water or aqueous vehicles which advantageously contain suspending agents, for example, methylcellulose, acacia, polyvinylpyrrolidone, polyvinyl alcohol and the like.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations are preferably administered intravenously, although administration may also be effected by means of subcutaneous, intramuscular, or intradermal injection. The formulation should be sufficiently fluid that easy syringeability exists. Such preparations may conveniently be prepared by admixing the compound with water or a glycine buffer and rendering the resulting solution sterile and isotonic with the blood. Such preparations should be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Injectable formulations according to the invention generally contain from 0.1 to 5% w/v of active compound and are administered at a rate of 0.1 ml/min/kg.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, and combinations of two or more thereof. The active compound is generally present at a concentration of from 0.1 to 15% w/w, for example, from 0.5 to 2% w/w.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 to 0.2M concentration with respect to the said active compound.

Formulations suitable for transdermal administration may also be delivered by iontophoresis (see, for example, Pharmaceutical Research 3 (6), 318, (1986)) and typically take the form of an optionally buffered aqueous solution of the active compound. Suitable formulations comprise citrate or bis\tris buffer (pH 6) or ethanol/water and contain from 0.1 to 0.2M active ingredient.

The kappa opioid receptor agonist is administered in an anxiety-combatting amount. The dose can vary depending on the agonist selected for administration, the subject, the route of administration, and other factors. Preferably, the compound is administered in an amount of between about 0.1 ng/kg and 1 g/kg, and more preferably is administered in an amount of between about 0.01 μg/kg and 0.1 g/kg.

The invention is illustrated in greater detail in the following non-limiting examples. In the Examples, "g" means grams, "mg" means milligrams, "kg" means kilograms, "mm" means millimeters, "cm" means centimeters, "μm" means micrometers, "ml" means milliliters, "μl" means microliters, and "°C." means degrees Celsius.

EXAMPLE 1

Maintenance of Test Subjects

Male Sprague-Dawley rats (Harlan, Indianapolis, Ind.) weighing from 224 g to 340 g were housed 3 or 4 to a cage in a room maintained at 22°–23° C. under 12 hours light/12 hours dark conditions (lights on at 6 am). Rat chow and water were provided ad libitum.

One day prior to behavioral testing the test animals were moved to the testing room so that the handling of cages would be minimized on the test day. The testing room was maintained at the identical temperature and light/dark schedule as the colony room. Approximately 2 hours prior to testing the room lights were attenuated to the level maintained through testing.

EXAMPLE 2

Introduction of Anxiolytic Agents to Rats

Each animal was anesthetized with 2.0 ml/kg eqithesin solution intraperitoneally, with a methoxyflurane overlay applied when supplemental anesthesia was required. Following standard aseptic surgical procedures previously described in Myers et al., Chronic Methods:Intraventricular Infusion, Cerebrospinal Fluid Sampling and Push-Pull Perfusion, in 3 *Methods in Psychology* 281–315 (Academic Press, New York 1977), bilateral craniotomy holes were drilled over predetermined sites so that a thin-walled 23 gauge stainless steel guide tube could be lowered through the dura. The tubes were positioned just dorsal to the intended hippocampal injection sites using the stereotaxic coordinates AP −3.5, lateral 3.5 and DV −3.5 mm relative to bregma. See Paxinos et al., *The Rat Brain* (Academic Press, New York 1982).

After 3–4 anchor screws were placed in the calvarium, cranioplastic cement was packed around the cannulae-pedestal assembly. A 27 gauge stylet of the same length as the guide was inserted in the tube to prevent its occlusion. A protective cap was screwed onto the pedestal. A recovery period of at least seven days elapsed before the beginning of the experiments.

EXAMPLE 3

Drugs and Experimental Groups

Subjects were divided into four groups. The first group received either U-50,488H (trans-3,4-dichloro-N-methyl-N-[2-1-pyrrolidinyl)cyclohexyl]benzene-acetamide methanesulfonate hydrate or saline vehicle intraperitoneally 20 minutes prior to testing. Drugs were delivered in a saline vehicle; dosages are as given in the figures. The second group received Naloxone or saline vehicle i.p. 35 minutes prior to testing and 15 minutes prior to i.p. administration of U-50,488H (the compound of Formula III) or saline vehicle. U-50,488H was purchased as the methane sulfonate from Research Biochemicals, Inc., One Strathmore Road, Natick, Mass., 01760-2418 U.S.A. (Tel. (508) 651–8151). The third group received bilateral intrahippocampal injections of Nor-Binaltorphine (Nor-BNI) or distilled water vehicle over a 5 minute period between 15 and 20 minutes prior to testing. Injections were carried out as described in Example 4. U-50,488H or saline vehicle was administered i.p. immediately following the first bilateral hippocampal injection and immediately preceding the second. The fourth group received intrahippocampal and i.p. vehicle only; these injections coincided with appropriate time points as described above for group three. Following the injections each rat was returned to its cage until the time of testing.

EXAMPLE 4

Microinjections into the Hippocampus

A solution of Nor-BNI was prepared each day by dissolving it in filtered (22 μm) distilled water. The solution was loaded into a 10 μl Hamilton microliter syringe affixed to a length of PE-20 tubing to which a 27 gauge injection needle was attached. A 1.0 μl microinjection was delivered to each rat at a rate of 1 μl/minute using a Harvard Apparatus Model 11 infusion pump. To verify the delivery of the 1.0 μl volume, a small bubble was introduced into the PE tubing and followed for a distance precalibrated to equal 1.0 μl. Following each injection the needle remained in place for an additional minute in order to minimize reflux.

EXAMPLE 5

Open Field Testing Apparatus

An open field was constructed consisting of a ¾ inch plywood box of dimensions 60 cm×60 cm×60 cm with an open top. The box was painted with a metallic color paint with a grid formed of black tape on the floor of the box. Each grid square was approximately 15 $cm^2$ and represented one locomotor unit.

EXAMPLE 6

Behavioral Testing Apparatus

An elevated plus-maze test as described and characterized in Pellow et al., Validation of Open:Closed Entries in an Elevated Plus-Maze as a Measure of Anxiety in the Rat, *J. Neuroscience Methods* 14:149–167 (1985), was employed. The plus-maze apparatus, elevated to a height of 50 cm above the floor, consists of two open arms, which are simply raised platforms, and two closed arms, which are enclosed on three sides with an open roof. The arms are arranged at right angles so that the two open arms oppose each other and the two closed arms oppose each other. The maze was constructed of ¾ inch marine plywood and finished with several coats of polyurethane. One-quarter inch plexiglass runways lining the open and closed arms were installed and changed following each test animal so that a test rat could not follow the scent track of the previous rat.

EXAMPLE 7

Behavioral Testing Procedure

Rats were randomly allocated to each experimental group. Individual rats from each group were tested on the same day to control for day to day environmental differences (e.g. cage changes, room cleaning, etc.) that may influence behaviors being tested.

Testing was performed under dimmed light conditions between 9 am and 12 noon with each rat being tested only once. At time of testing each animal was placed in the center of the open field and spontaneous locomotor activity was measured by recording the number of grid squares entered (all 4 paws) for a period of 5 minutes. The animal was then immediately placed on the center of the elevated plus-maze facing an open arm. Open arm entries, closed arm entries, and time spent in each arm type was recorded for 5 minutes. The ratio of number of entries into the open arms over the total number of entries into all arms was calculated. This ratio is considered to be a reflection of the level of fear-induced inhibition to enter the open arms and can be compared to the degree of stress or anxiety experienced by the animal being tested.

EXAMPLE 8

Histological and Statistical Analysis of Specimens

At the conclusion of the experiments, each rat was given an overdose of sodium pentobarbital and perfused transcardially with normal saline followed by 10% buffered formalin. After the brain was removed, sections were cut in the coronal plane at 40 μm on a cryotome, mounted and stained for nissl. Anatomical maps of the sites of microinjection were then constructed after their identification by light microscopy.

The results were analyzed statistically by paired students T-tests on the differences between control and treatment groups for all measures and doses. Results were considered to be statistically significant at the level of $p<0.05$.

EXAMPLE 9

Locomotor Activity of U-50,488H Injected Rats in Open Field Testing

The open field is a behavioral test widely used to measure components of exploratory activity such as rearing, hole poking, and the like, but can also be utilized for the determination of sedative effects of compounds by measuring spontaneous locomotor activity. FIG. 1 shows the results of open field testing for rats receiving different 3 doses of U-50,488H tested compared to the saline control group. There were no measurable differences in the 5 minute open field test of locomotor activity for all groups. This finding for spontaneous locomotor behavior between all groups is consistent with that expected from a compound which demonstrates no sedative effects.

EXAMPLE 10

Locomotor Activity of Rats Injected with U-50,488H in Plus-Maze Testing

Figure 2:
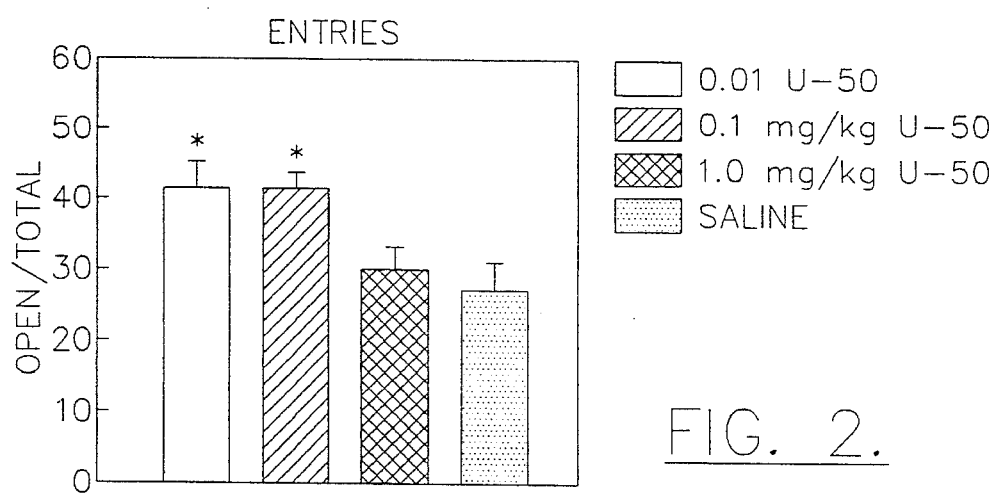
FIG. 2 is a bar graph showing the number of entries onto the open arm of a plus-maze of rats administered one of three different dosages of U-50,488H or saline.

The number of times a rat will enter an open arm of a plus-maze compared to the total number of entries in all arms (expressed as a percentage) is thought to measure the willingness of an animal to explore an environment that may be perceived as threatening. This measure can also reflect sedative effects of the test compound in that drugs known to cause sedation will lower this percentage. FIG. 2 illustrates the dose-dependent effects of U-50,488H on the percentage of open/total arm entries on the elevated plus-maze. Significant (95% confidence level) differences were observed in the percentage of open/total entries for the 0.01 and 0.1 mg/kg U-50,488H treatment groups. The treatment group receiving 1.0 mg/kg showed no difference compared to the saline control group. A compound with sedative actions causes a reduction in the total number of entries by this plus-maze measure. No U-50,488H-treated experimental groups produced an open arm/total arm ratio below that of the saline control. This result provides further evidence that sedative effects at the doses tested are absent.

EXAMPLE 11

Anxiety Levels of U-50,488H-Injected Rats in Plus-Maze Testing

Figure 3:
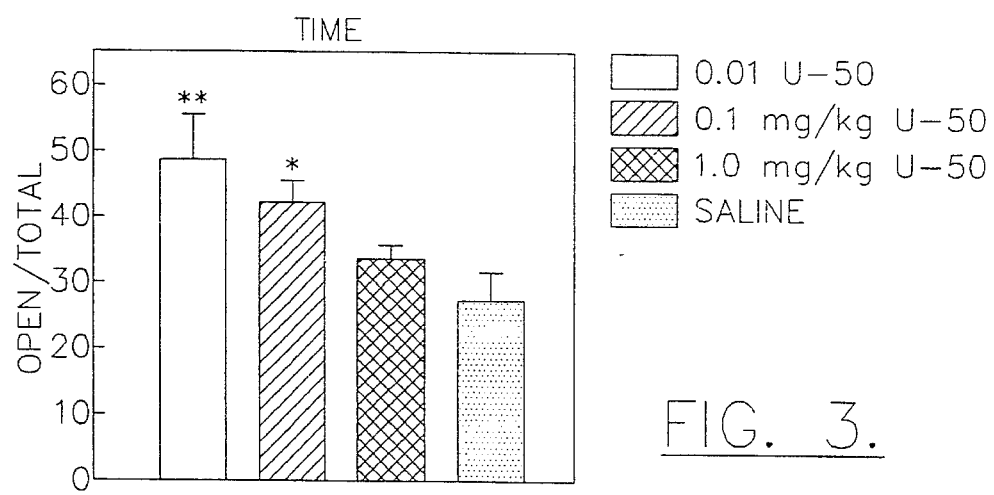
FIG. 3 is a bar graph showing the time spent on the open arm of a plus-maze by rats administered one of three different dosages of U-50,488H or saline.

In elevated plus-maze testing, the key index for measuring anxiety is the percentage of time spent on the open arm to the total time on all arms. There is a direct relationship between the relative amount of time spent on the open arms and the anxiolytic efficacy of a given compound. FIG. 3 reveals an inverse dose-dependent response in the percentages of open/total time for each dose. This effect was most significant (99% confidence level) for the 0.01 mg/kg dose.

EXAMPLE 12

Activity of Antagonists Against U-50,488H

Nor-binaltorphine (nor-BNI) is a highly selective antagonist of the kappa subtype of opioid receptor. Because it was hypothesized that peripherally administered U-50,488H was acting predominantly within the hippocampus to elicit its anxiolytic effects, it would follow that bilateral injections of a selective antagonist to U-50,488H (nor-BNI) directly into the hippocampal formation may ameliorate this effect.

As previously mentioned, the measurement on the plus-maze most sensitive to the detection of anxiolysis is the ratio of open/total time spent on the maze, whereas the percentage of open/total entries is more a reflection of locomotor activity or willingness to explore novelty. Therefore, the reversal of U-50,488H-induced anxiolysis would be most evident in the open/total time measurement.

Figure 4:
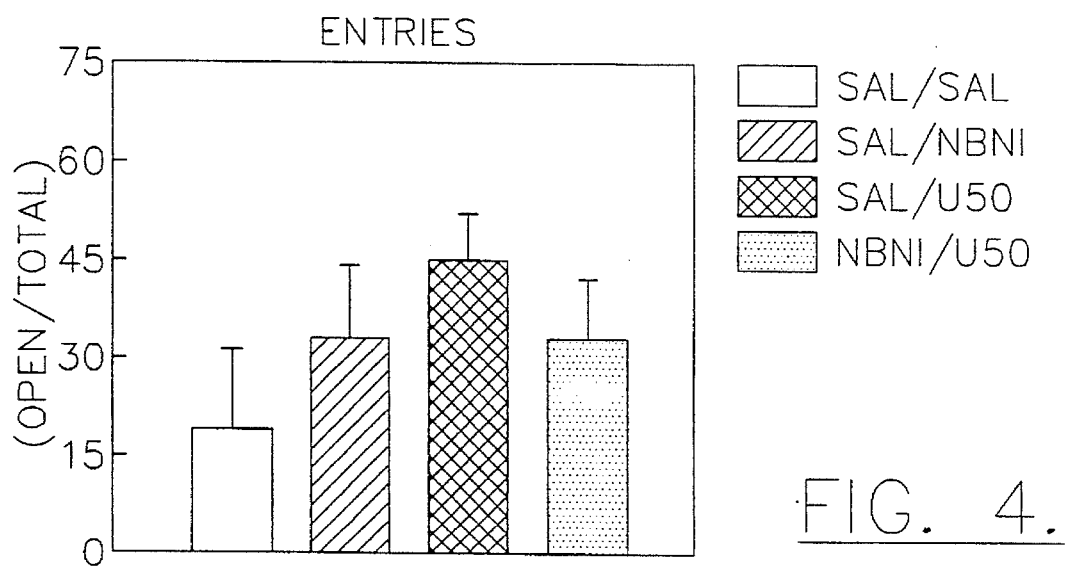
FIG. 4 is a bar graph showing the number of entries onto the open arm of a plus-maze of rats administered peripheral saline and intrahippocampal saline, peripheral saline and intrahippocampal Nor-BNI, peripheral U-50,488H and intrahippocampal saline, or peripheral U-50,488H and intrahippocampal Nor-BNI.

As can be seen in FIG. 4, nor-BNI injected directly into the hippocampus with or without peripheral U-50,488H (0.1 mg/kg U-50,488H) had little to no effect on open/total entries compared with saline control values. Intrahippocampal saline and peripheral U-50,488, however, demonstrated a significant increase (95% confidence level) in the open/total entries. This results confirms the findings of Example 11 that indicate that U-50,488H by itself has potent anxiolytic properties, even following intrahippocampal injections of vehicle.

Figure 5:
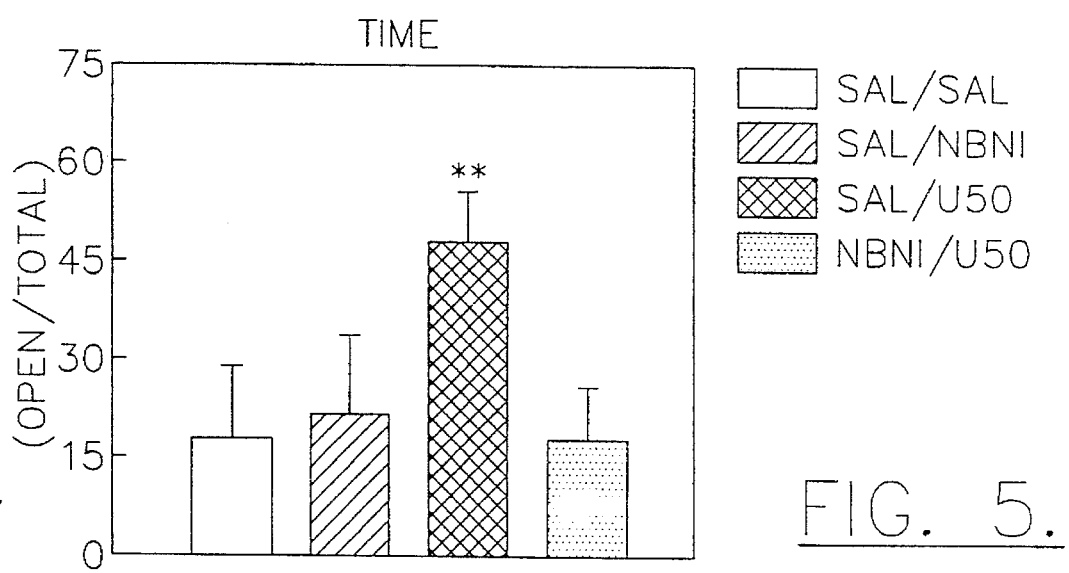
FIG. 5 is a bar graph showing the time spent on the open arm of a plus-maze by rats administered peripheral saline and intrahippocampal saline, peripheral saline and intrahippocampal Nor-BNI, peripheral U-50,488H and intrahippocampal saline, or peripheral U-50,488H and intrahippocampal Nor-BNI.

FIG. 5 presents data for the open/total time percentage for rats (a) injected intrahippocampally with Nor-BNI and i.p. with U-50,488H, (b) injected intrahippocampally with Nor-BNI and i.p. with vehicle, (c) injected intrahippocampally with vehicle and i.p. with U-50,488H, and (d) injected intrahippocampally with vehicle and i.p. with vehicle. The data reveals a significant difference (99% confidence level) in anxiolytic effect from saline control for the peripheral U-50,488H/central saline treatment group. Of greatest interest is the complete reversal of the U-50,488H effect by the bilateral intrahippocampal injection of the antagonist Nor-BNI. Also note that Nor-BNI by itself had no effect on behavior.

These results provide compelling evidence that U-50,488H is endowed with potent anxiolytic properties. The data suggest that the anxiolytic effects of U-50,488H are mediated by a mechanism involving the kappa subtype of opioid receptor. Further, the site of action for this effect can, in large part, be localized to the hippocampal formation. These conclusions are supported by the demonstration that the anxiolysis induced by U-50,488H can be completely reversed following bilateral injections, directly into the hippocampal formation, of the selective kappa opioid antagonist nor-BNI, and that nor-BNI by itself has no measurable effects.

The foregoing examples are illustrative of the present invention, and are not to be construed as limiting thereof. The invention is defined by the following claims, with equivalents of the claims to be included therein.

That which is claimed is:

1. A method of treating anxiety in subjects in need of such treatment comprising administering to said subject a kappa opioid receptor agonist in an effective anxiety-combatting amount, wherein said kappa opioid receptor agonist is a compound of the formula:

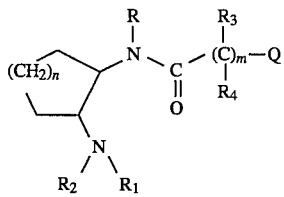 (I)

wherein

R is C1 to C3 alkyl;

$R_1$ is C1 to C3 alkyl, and $R_2$ is C1 to C6 alkyl, —CH$_2$CF$_3$, C3 to C6(allylic)alkenyl, C2 to C5 hyroxylalkyl, C3 to C6 cycloalkyl, C3 to C4 cycloaklylmethyl, phenyl C1 to C3 alkyl, or alternatively $R_1$ and $R_2$ together with the nitrogen atom to which they are bonded form a saturated, monocyclic, heterocyclic ring containing only carbon and nitrogen ring atoms and containing from 3 to 4 carbon atoms; said saturated monocyclic heterocylic ring being optionally substituted in the 3 position of the ring with hydroxy, C1 to C3 alkyl, C1 to C3 alkyloxy, or C1 to C3 alkanoyloxy;

$R_3$ is hydrogen or methyl;

$R_4$ is hydrogen or methyl, or $R_3$ and $R_4$ together with the carbon atom to which they are bonded form a cyclopropylene ring;

m is 1 to 4;

n is 2 to 4;

Q is 1-naphthyl, 2-naphthyl or a moiety of formula II

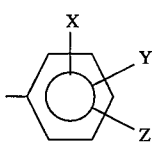 (II)

wherein each of X, Y and Z is hydrogen, a halogen having an atomic number of from 9 to 35, trifluoromethyl, C2 to C3 alkyl, C1 to C3 alkyloxy, azido or phenyl, and at least one of X, Y and Z is a substituent other than hydrogen, and when one of X, Y and Z is azido, phenyl, C1 to C3 alkyloxy or trifluoromethyl, the remaining X, Y and Z moieties are hydrogen, and the pharmaceutically acceptable salts thereof.

2. A method of treating anxiety according to claim 1 wherein:

R is C1 to C3-alkyl;

R1 is C1 to C3-alkyl, and R2 is C1 to C6-alkyl, —CH2CF3, C3 to C6-(allylic)alkenyl, C2 to C5-hydroxyalkyl, C3 to C6-cycloalkyl, C3 to C4-cycloalkylmethyl, phenyl-C1 to C3-alkyl, or alternatively R1 and R2 together with the nitrogen atom to which they are bonded form a saturated, monocyclic, heterocyclic ring containing only carbon and nitrogen ring atoms and containing from 3 to 4 carbon atoms; said saturated monocyclic heterocyclic ring being optionally substituted in the 3-position of the ring with hydroxy, C1 to C3 alkyl, C1 to C3-alkyloxy, or C1 to C3-alkanoyloxy;

R3 and R4 are each hydrogen;

n is 2;

m is 1;

Q is a moiety of formula II

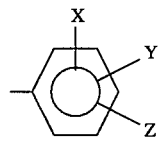 (II)

wherein at least one of X, Y and Z is a halogen having an atomic number of from 9 to 35; and pharmaceutically acceptable salts thereof.

3. A method of treating anxiety according to claim 1 wherein said compound is in the trans-configuration, and wherein:

R is methyl;

R1 is C1 to C3-alkyl, and R2 is C1 to C6-alkyl, —CH2CF3, C3 to C6-(allylic)alkenyl, C2 to C5-hydroxyalkyl, C3 to C6-cycloalkyl, C3 to C4-cycloalkylmethyl, phenyl-C1 to C3-alkyl, or alternatively R1 and R2 together with the nitrogen atom to which they are bonded form a saturated, monocyclic, heterocyclic ring containing only carbon and nitrogen ring atoms and containing from 3 to 4 carbon atoms; said saturated monocyclic heterocyclic ring being optionally substituted in the 3-position of the ring with hydroxy, C1 to C3 alkyl, C1 to C3-alkyloxy, or C1 to C3-alkanoyloxy;

R3 and R4 are each hydrogen;

n is 2;

m is 1; and

Q is 3,4 dichlorophenyl; and the pharmaceutically acceptable salts thereof.

4. A method of treating anxiety according to claim 1 wherein:

R is C1 to C3-alkyl;

R1 and R2 together with the nitrogen atom to which they are bonded form a saturated monocyclic heterocyclic ring containing from 3 to 4 ring carbon atoms;

R3 and R4 are each hydrogen;

n is 2;

m is 1, and

Q is a moiety of formula II

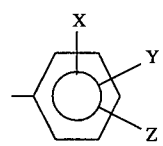 (II)

wherein at least one of X, Y and Z is a halogen having an atomic number of from 9 to 35, or azido; and pharmaceutically acceptable salts thereof.

5. A method of treating anxiety according to claim 1 wherein said compound is trans-N-[2-(1-pyrrolidinyl)cyclohexyl]-N-methyl-2-(3,4-dichlorophenyl) acetamide or a pharmaceutically acceptable salt thereof.

6. A method of treating anxiety according to claim 1 wherein:

R is C1 to C3-alkyl;

R1 is C1 to C3-alkyl, and R2 is C1 to C6-alkyl, —CH2CF3, C3 to C6-(allylic)alkenyl, C2 to C5-hydroxyalkyl, C3 to C6-cycloalkyl, C3 to C4-cycloalkylmethyl, phenyl-C1 to C3-alkyl, or alternatively R1 and R2 together with the nitrogen atom to which they are bonded form a saturated, monocyclic, heterocyclic ring containing only carbon and nitrogen ring atoms and containing from 3 to 4 carbon atoms; said saturated monocyclic heterocyclic ring being optionally substituted in the 3-position of the ring with hydroxy, C1 to C3 alkyl, C1 to C3-alkyloxy, or C1 to C3-alkanoyloxy;

R3 and R4 are each hydrogen;

n is 2 to 4;

m is 1; and

Q is a moiety of formula II

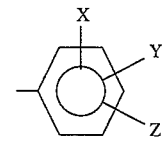
(II)

wherein at least one of X, Y and Z is a halogen having an atomic number of from 9 to 35; and pharmaceutically acceptable salts thereof.

* * * * *